US 11,872,137 B2

United States Patent
Strohkirch et al.

(10) Patent No.: US 11,872,137 B2
(45) Date of Patent: Jan. 16, 2024

(54) UNICOMPARTMENTAL ANKLE PROSTHESIS

(71) Applicant: WRIGHT MEDICAL TECHNOLOGY, INC., Memphis, TN (US)

(72) Inventors: Terrance W. Strohkirch, Memphis, TN (US); Shawn E. McGinley, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 118 days.

(21) Appl. No.: 17/660,047

(22) Filed: Apr. 21, 2022

(65) Prior Publication Data

US 2022/0395377 A1 Dec. 15, 2022

Related U.S. Application Data (60) Provisional application No. 63/210,621, filed on Jun. 15, 2021.

(51) Int. Cl.
*A61F 2/42* (2006.01)
*A61F 2/30* (2006.01)

(52) U.S. Cl.
CPC ........ *A61F 2/4202* (2013.01); *A61F 2/30771* (2013.01); *A61F 2002/3082* (2013.01); *A61F 2002/30227* (2013.01); *A61F 2002/30604* (2013.01); *A61F 2002/30878* (2013.01);

(Continued)

(58) Field of Classification Search
CPC ............ A61F 2/4202; A61F 2002/4205; A61F 2002/4207
See application file for complete search history.

(56) References Cited

U.S. PATENT DOCUMENTS

| | | |
|---|---|---|
| 3,839,742 A | 10/1974 | Link |
| 3,872,519 A | 3/1975 | Giannestras et al. |
| 3,886,599 A | 6/1975 | Schlein |

(Continued)

FOREIGN PATENT DOCUMENTS

| | | |
|---|---|---|
| CA | 2836651 | 3/2016 |
| EP | 2967697 | 4/2018 |

(Continued)

OTHER PUBLICATIONS

Extended European Search Report issued in connection with European Patent Application No. 22170009.9, dated Mar. 13, 2022, 8 pages.

(Continued)

*Primary Examiner* — Brian A Dukert
(74) *Attorney, Agent, or Firm* — DUANE MORRIS LLP (57) ABSTRACT

A partial ankle prosthesis includes a tibial component including a superior surface configured to be attached to a lower end of a patient's tibia; a poly component that is fixedly attached to the tibial component and includes a concave inferior surface of an anti-friction material; and a talar component including an inferior surface configured to be attached to a patient's talus and a single convex superior surface configured to mate with the inferior surface of the poly component; and the partial ankle prosthesis is configured to be implanted in a single compartment of a patient's ankle.

20 Claims, 8 Drawing Sheets

(52) U.S. Cl.
CPC ............... *A61F 2002/4207* (2013.01); *A61F 2310/00011* (2013.01)

(56) References Cited

U.S. PATENT DOCUMENTS

| | | | |
|---|---|---|---|
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,475,463 B2 | 7/2013 | Lian |
| 8,491,596 B2 | 7/2013 | Long et al. |
| 8,808,303 B2 | 8/2014 | Stemniski et al. |
| 8,911,444 B2 | 12/2014 | Bailey |
| 9,907,561 B2 | 3/2018 | Luna et al. |
| 10,034,678 B2 | 7/2018 | Park et al. |
| 10,039,558 B2 | 8/2018 | Park et al. |
| 10,206,688 B2 | 2/2019 | Park et al. |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |

(56) References Cited

U.S. PATENT DOCUMENTS

| | | |
|---|---|---|
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0106268 A1 | 5/2011 | Deffenbaugh et al. |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2015/0320567 A1 | 11/2015 | Terrill et al. |
| 2016/0135815 A1 | 5/2016 | Loring et al. |
| 2016/0262903 A1* | 9/2016 | West .................. A61F 2/4202 |

FOREIGN PATENT DOCUMENTS

| | | |
|---|---|---|
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009158522 | 12/2009 |
| WO | WO 2010099142 | 9/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |

OTHER PUBLICATIONS

Search report issued for European patent application No. 13198280 dated Feb. 5, 2014.
International Search Report for International patent application No. PCT/US2014/027448 dated Jul. 7, 2014.
International Preliminary Report on Patentability issued for International patent application No. PCT/US2014/027448, dated Sep. 15, 2015, 8 pages.
Partial European Search Report issued in connection with European patent application No. 14768333.8, dated Oct. 26, 2016, 6 pages.
Patent Examination Report No. 1 issued in connection with Australian patent application No. 2015202080, dated Jul. 5, 2016, 4 pages.
First Office Action issued for Japanese patent application No. 2016-117842, dated Sep. 12, 2017, 5 pages.
First Office Action issued in connection with corresponding Japanese Patent Application No. 2020-016447, dated Apr. 6, 2021, 4 pages.
Office Action in corresponding Canadian Patent Application No. 2,904,652, dated Jun. 2, 2020, 6 pages.
First Examination Report issued in corresponding Australian Patent Application No. 2019213412, dated Sep. 3, 2020, 5 pages.
First Office Action in corresponding Canadian Patent Application No. 2,904,652, dated Jan. 28, 2020, 5 pages.
Final Office Action issued in connection with corresponding Japanese Patent Application No. 206-502443, dated May 15, 2018, 3 pages.
Extended European Search Report issued in connection with corresponding European Patent Application No. 18160378.8, dated Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, dated Sep. 3, 2018, 3 pages.
Examination Report No. 1 issued in connection with corresponding Australian Patent Application No. 20182000073, dated Dec. 24, 2018, 3 pages.
First Office Action in corresponding Japanese Patent Application No. 2018-092289, dated Mar. 5, 2019, 2 pages.
Extended European Search Report and Opinion in connection with European Patent Application No. 14768333.8, dated Jan. 30, 2017, 10 pages.

* cited by examiner

UNICOMPARTMENTAL ANKLE PROSTHESIS

CROSS-REFERENCE TO RELATED APPLICATION

This application claims priority under 35 U.S.C. § 119(e) to U.S. Provisional Application No. 63/210,621, filed Jun. 15, 2021, the entirety of which is incorporated by reference herein.

BACKGROUND

1. Field of Disclosure

This disclosure relates to prosthetics generally, and more specifically to prostheses for a unicompartmental ankle replacement.

2. Description of the Related Art

The ankle is a joint that acts much like a hinge. The joint is formed by the union of three bones. The ankle bone is the talus. The top of the talus fits inside a socket that is formed by the lower end of the tibia, and the fibula, the small bone of the lower leg. Arthritis, bone degeneration, and/or injury can cause ankle joint deterioration resulting in pain, reduced range of motion, and decreased quality of life. In many cases, physicians are recommending ankle replacement surgery with a prosthetic implant as an option. Consequently, improved prostheses for ankle replacements are desirable.

Figure 1:
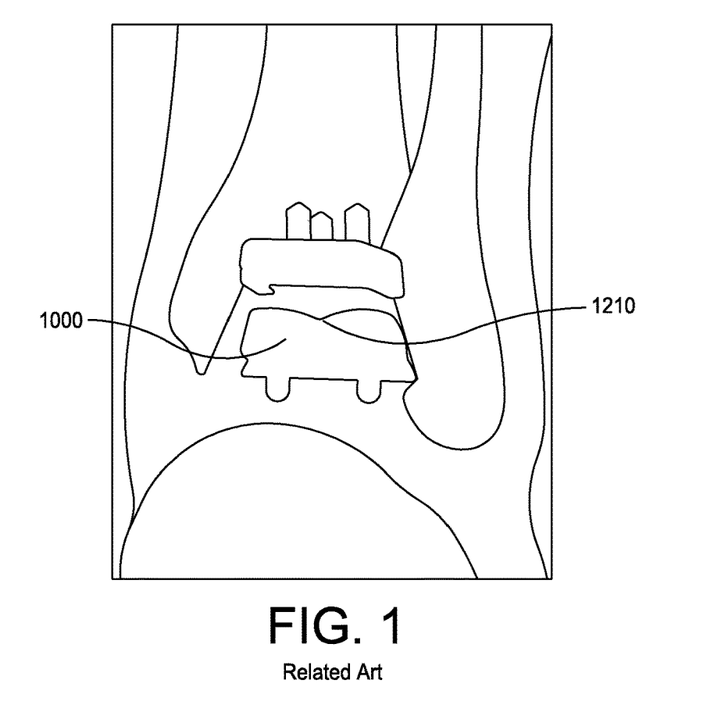
FIG. 1 is a representation of a radiograph of an ankle including an ankle replacement prosthesis according to the related art.
Figure 2:
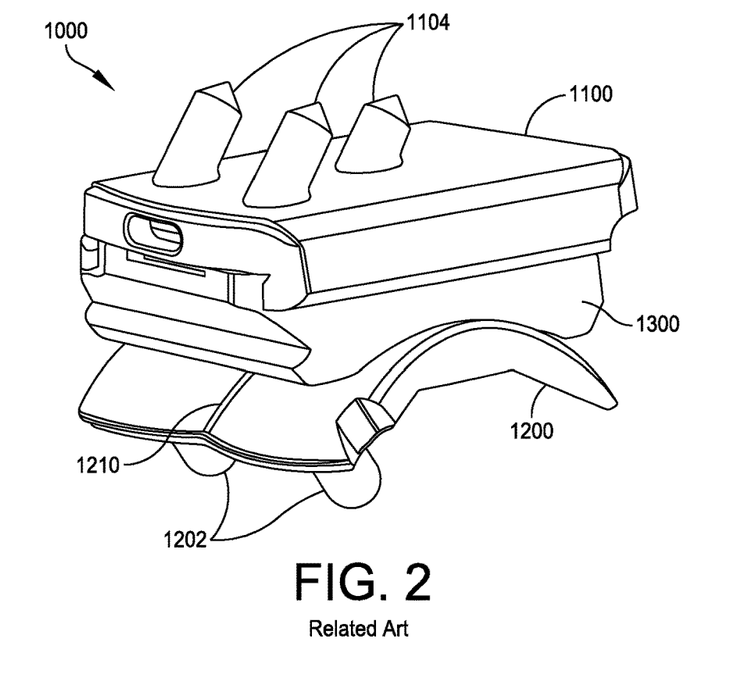
FIG. 2 is an isometric view of an ankle replacement prosthesis in accordance with the related art.

FIG. 1 is a representation of a radiograph of a front of a patient's right ankle including a complete ankle replacement prosthesis 1000 such as the Infinity™ Total Ankle Replacement from Wright Medical, according to the related art. FIG. 2 is an isometric view of the ankle replacement prosthesis 1000 shown in FIG. 1. As shown, the ankle replacement prosthesis 1000 includes a tibial implant 1100, a talar implant 1200, and a poly implant 1300. Upon completion of an ankle replacement procedure, the tibial implant 1100 is connected to the tibia, with pegs 1104 located within peg holes in the resected tibia. The talar implant 1200 is connected to the talus, with talar dome anterior pegs 1202 located within holes in the talus. The poly implant 1300 is inserted and located between the tibial implant 1100 and the talar implant 1200.

In such a system, the tibial implant 1100, conventionally made of titanium, covers the bottom (distal end) of the shinbone (tibia) to provide a large footprint for fixation and minimize implant subsidence. The poly implant 1300, conventionally made of polyethylene, acts as the articulating surface of the distal shinbone (tibia) and glides along the contours of the ankle i.e., the talar implant 1200, a highly polished dual metal dome structure. The talar implant 1200 replaces the proximal end (top) of the talus (ankle) bone. The talar implant 1200 acts as the surface upon which the poly implant 1300 glides.

As shown in FIGS. 1 and 2, the top of the talar implant 1200 is shaped with two adjacent rounded convex surfaces that are separated by a sulcus or groove 1210. This construction allows for full freedom of movement in the patient's ankle joint while providing the needed dynamic stabilization.

This total ankle system is intended to give a patient limited mobility by reducing pain, restoring alignment, and replacing the flexion and extension movement in the ankle joint and is indicated for patients with ankle joints damaged by severe rheumatoid, posttraumatic, or degenerative arthritis. However, this total ankle system does not address the need for a partial replacement of the ankle joint where either only the medial or lateral side is degenerative or has a defect.

SUMMARY OF THE INVENTION

To overcome the problems described above, preferred embodiments of the present disclosure provide a first step or bridge to conventional treatment and a total ankle in a partially degenerative ankle or an ankle with a unicompartment defect. A unicompartmental ankle prosthesis of the present disclosure would cover either the medial or lateral side of an ankle preserving more bone and being less invasive than a total ankle replacement.

A partial ankle prosthesis includes a tibial component including a superior surface configured to be attached to a lower end of a patient's tibia; a poly component that is fixedly attached to the tibial component and includes a concave inferior surface of an anti-friction material; and a talar component including an inferior surface configured to be attached to a patient's talus and a single convex superior surface configured to mate with the inferior surface of the poly component; and the partial ankle prosthesis is configured to be implanted in a single compartment of a patient's ankle.

The superior surface of the tibial component can includes an outwardly projecting peg configured to fit into a hole in the patient's tibia. The anterior surface of the talar component can include a peg configured to fit into a hole in the patient's talus.

In an embodiment, the superior surface of the talar component can have only one continuous concave curvature both longitudinally between opposite anterior and posterior ends and laterally between opposite medial and lateral sides. The anterior surface of the talar component may advantageously define one or more grooves so as to provide additional surface area and thereby increase bone adhesion. The talar component may also define one or more a notches arranged on the prosthesis so as to interface with a surgical assembly tool.

The partial ankle prosthesis can further include a bioactive coating on a surface of the tibial component and/or the talar component that interfaces with a patient's bone.

An inferior surface of the talar component can be curved and configured to attach to a talar dome of the talus. The inferior surface of the talar component can be substantially flat.

The above and other features, elements, characteristics, steps, and advantages of the present invention will become more apparent from the following detailed description of preferred embodiments of the present invention with reference to the attached drawings.

BRIEF DESCRIPTION OF THE DRAWINGS

The description of the exemplary embodiments disclosed herein are intended to be read in connection with the accompanying drawings, which are to be considered part of the entire written description. All drawing figures are schematic illustrations and are not intended to show actual dimensions or proportions.

DETAILED DESCRIPTION OF PREFERRED EMBODIMENTS

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," "extending" projecting" etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Figure 3:
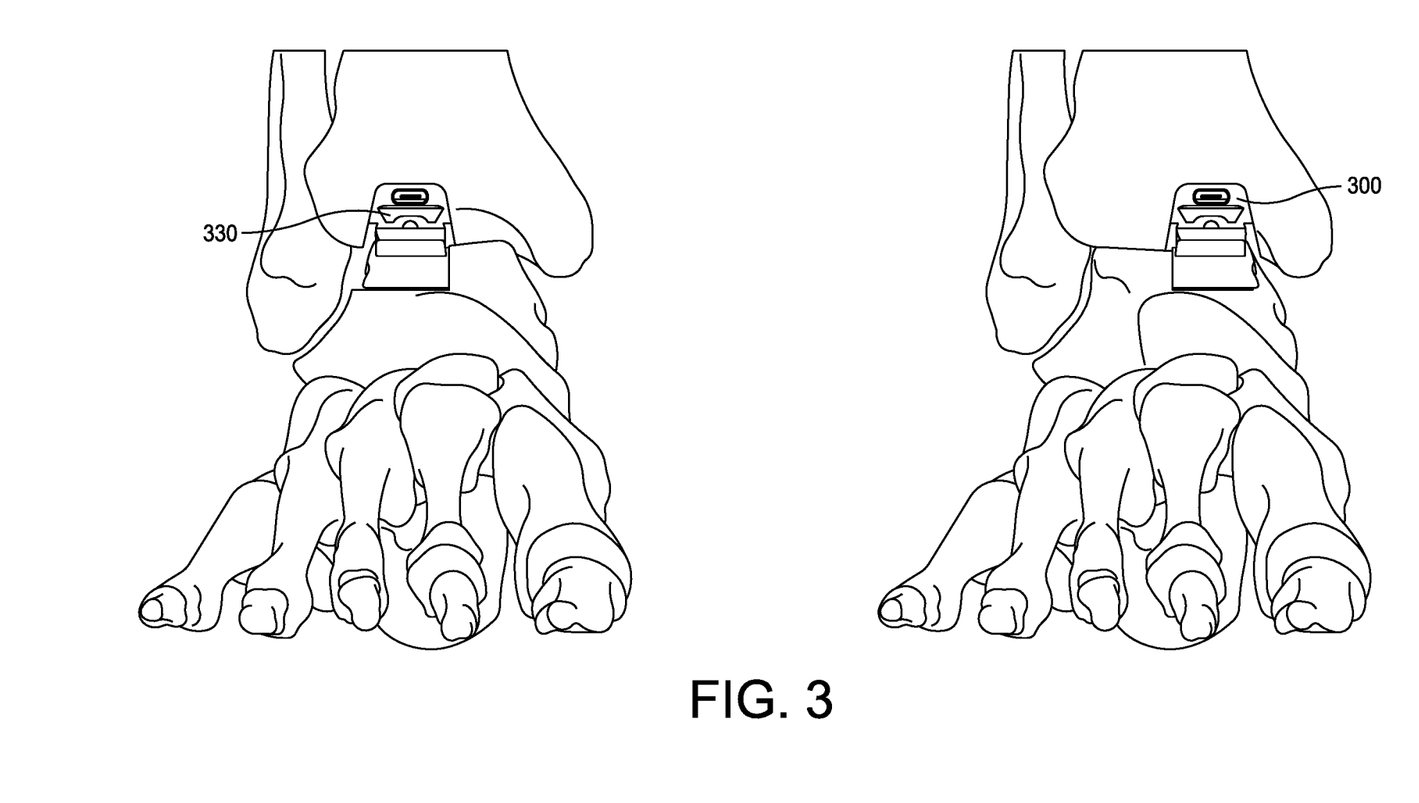
FIG. 3 is an image showing two embodiments of the present disclosure.
Figure 4:
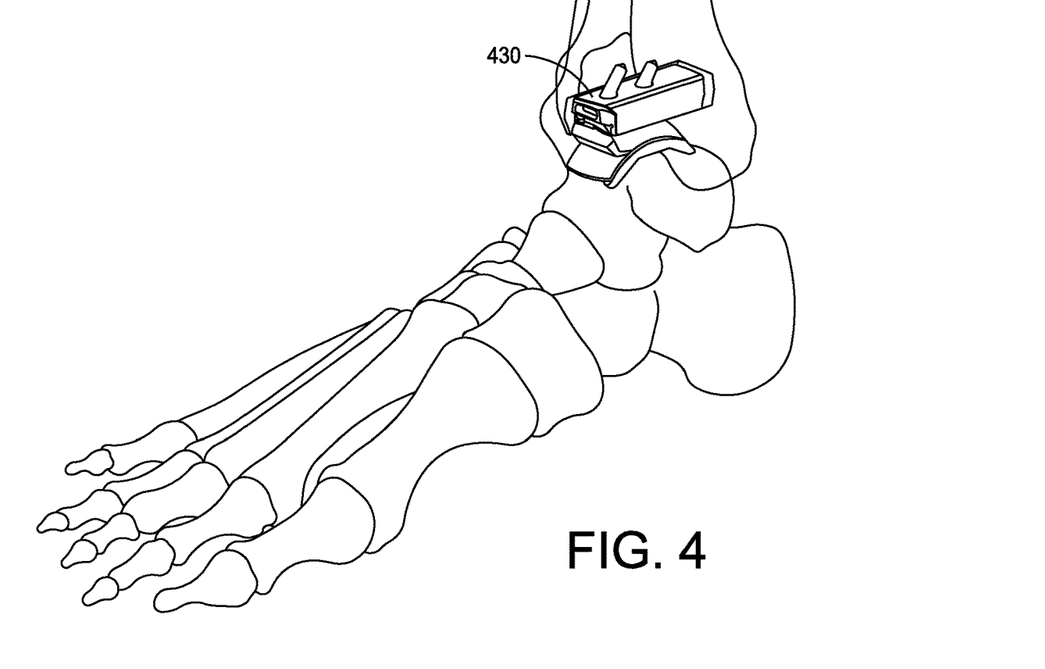
FIG. 4 is an isometric view representing a lateral unicompartmental ankle prosthesis in an ankle.
Figure 5:
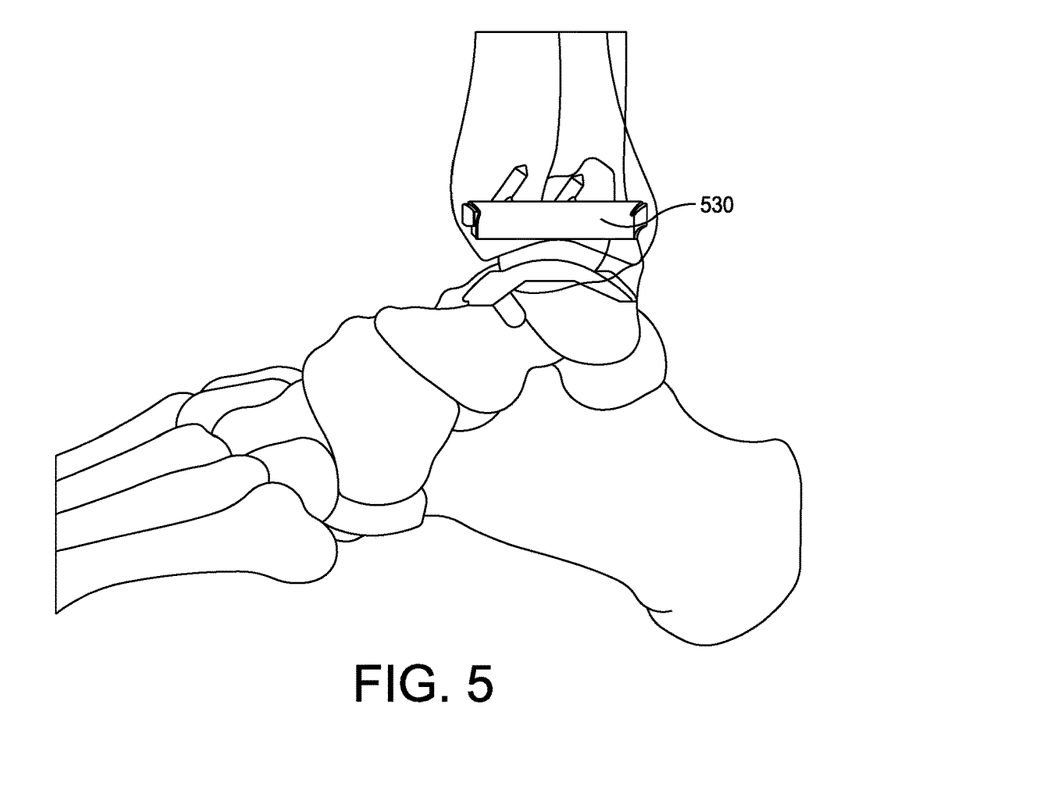
FIG. 5 is a side view representing a lateral unicompartmental ankle prosthesis in an ankle.

FIG. 3 is an image showing two embodiments of the present disclosure. In FIG. 3, two side-by-side skeletal images of a patient's right foot represent a medial unicompartmental ankle prosthesis 300 and a lateral unicompartmental ankle prosthesis 330 installed in a corresponding medial or lateral side of an ankle. FIG. 4 is an isometric view and FIG. 5 is a side view representing a corresponding lateral unicompartmental ankle prosthesis 430, 530 in an ankle. The structures of the medial unicompartmental ankle prosthesis 300 and the lateral unicompartmental ankle prosthesis 330 are mirror images of each other.

Figure 6:
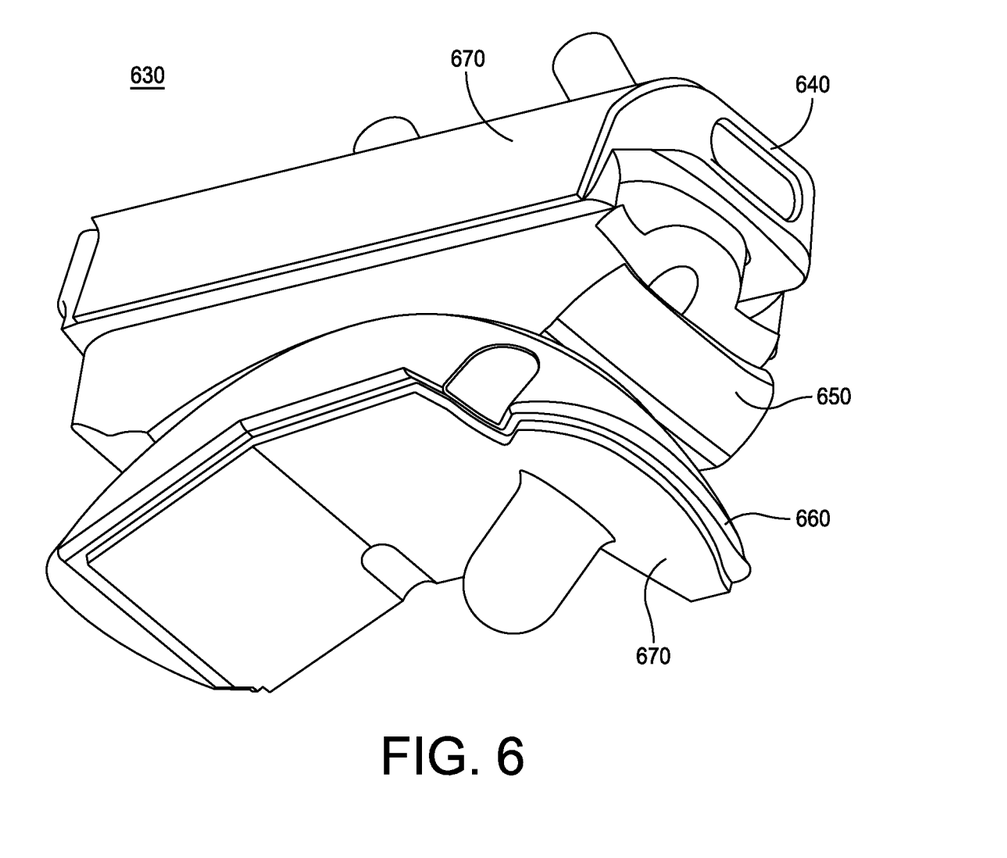
FIG. 6 is a bottom isometric view of a three-piece lateral unicompartmental ankle prosthesis.

FIG. 6 is a bottom isometric view of a three-piece lateral unicompartmental ankle prosthesis 630 that includes a tibial component 640, a talar component 660, and a poly component 650. Optionally, as shown, the bone contacting surfaces of the unicompartmental ankle prosthesis 630 can be coated with a bioactive coating 670 to enhance bone growth and adhesion to the components while minimizing infection. That is, the top and side surfaces of the tibial component 640 and the bottom surface of the talar component 660 can be coated with the bioactive coating 670. The bioactive coating 670 can include beads, a plasma spray, a lattice foam structure, etc. This coating can be around 1 mm thick and located where there is a bone to implant interface.

Figure 7:
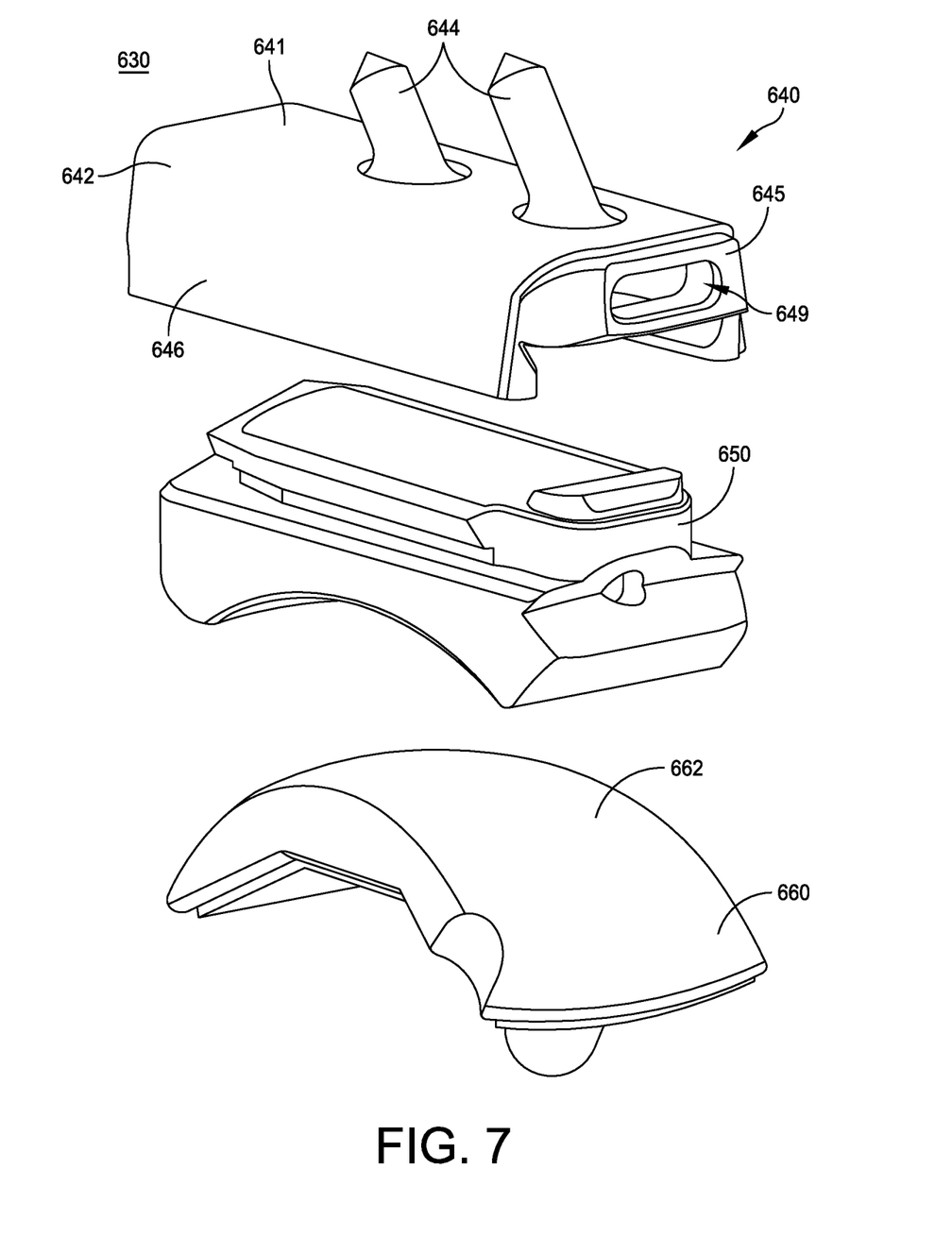
FIG. 7 is an exploded view of the lateral unicompartmental ankle prosthesis of FIG. 6.
Figure 8:
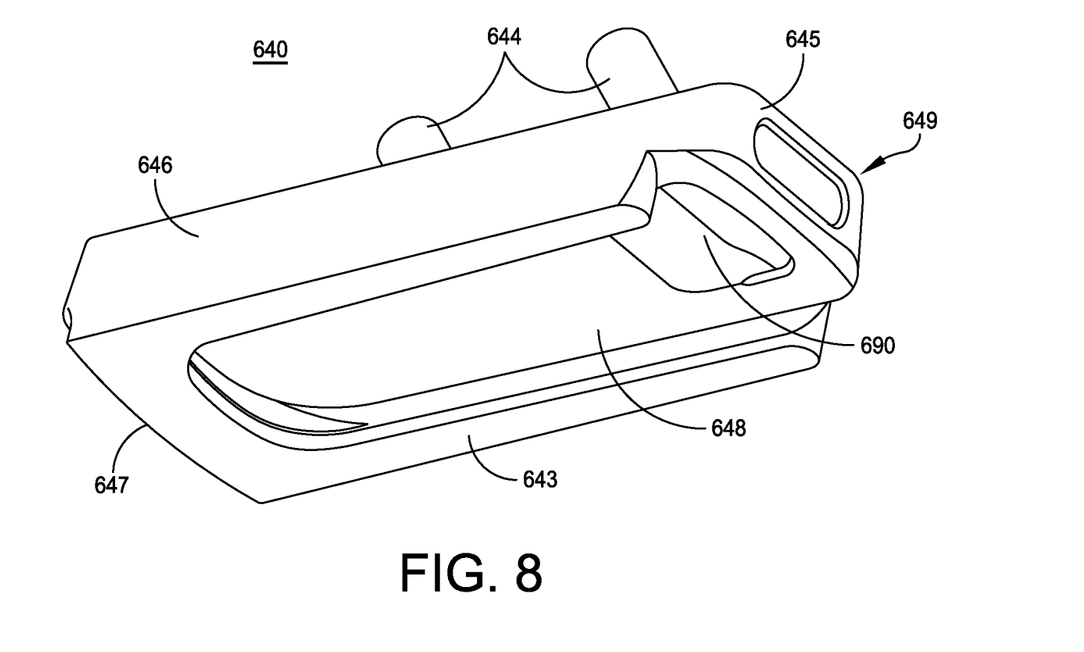
FIG. 8 is an underside view of a tibial component.

FIG. 7 is an exploded view of the lateral unicompartmental ankle prosthesis 630 of FIG. 6. FIG. 8 is an underside view of the tibial component 640 shown without the bioactive coating 670. As shown in FIGS. 7 and 8, the tibial component 640 can have a substantially rectangular cuboid body 642 with one or more pegs 644 protruding out of a superior side 641 of the body 642. The pegs 644 are configured to be received in holes formed in the tibia. The tibial component 640 can also include two opposed shoulders 646 that are curved or chamfered relative to the superior side 641 of the body 642. A recessed area or recess 648 extends posteriorly from an anterior face 645 to an insertion end (or posterior end) 647 along the inferior side 643 of the tibial component 640. The recess 648 can be configured to receive sides and a curved edge of a tibial tray impaction insert tool as a means for holding the tibial component 640 in place during insertion. Additionally, the sides of the recess 648 can be undercut and angled to receive and engage with a dovetail feature of the poly component 650.

Bone cement (not shown) can be applied to the superior 641, medial, and lateral sides of the body 642 while a face of the anterior side 645 and inferior side 643 remains free of any cement.

As shown, the tibial component 640 can also include an opening 649 in the anterior face 645 to a cavity 690 that joins with the recess 648. The opening 649 can be used as an interface for a surgical assembly tool and to view a top of the poly component 650 to verify correct installation and alignment.

The tibial component 640 can be made of a cobalt chrome alloy, stainless steel, titanium, titanium alloy, or any other suitable material. Optionally, the tibial component 640 can be made using an additive manufacturing process such as 3-D printing. Optionally, the tibial component 640 can be made to fit an individual patient.

Figure 9:
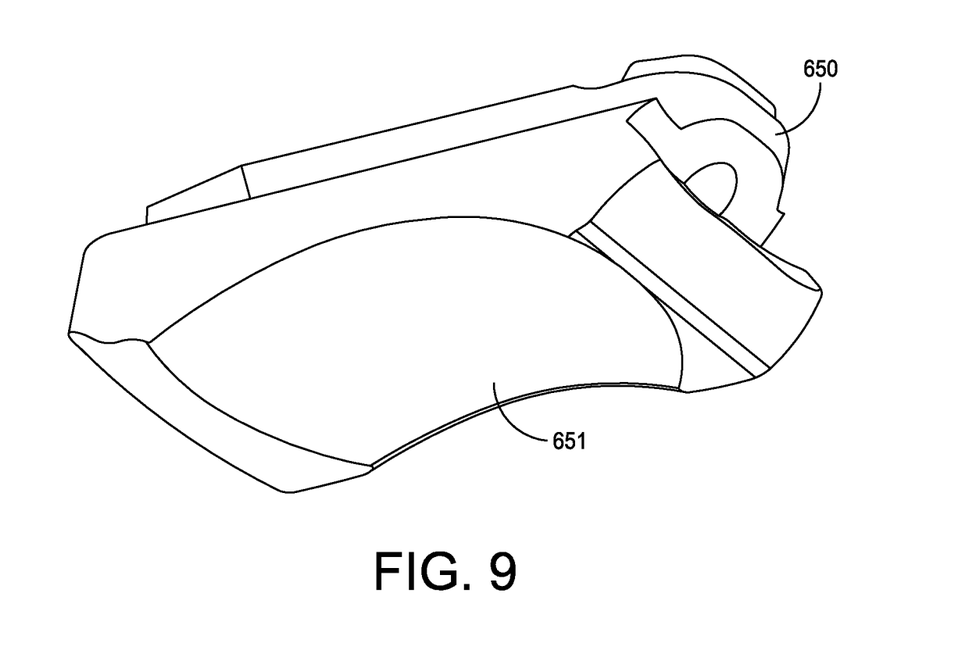
FIG. 9 is an underside view of a poly component.
Figure 10:
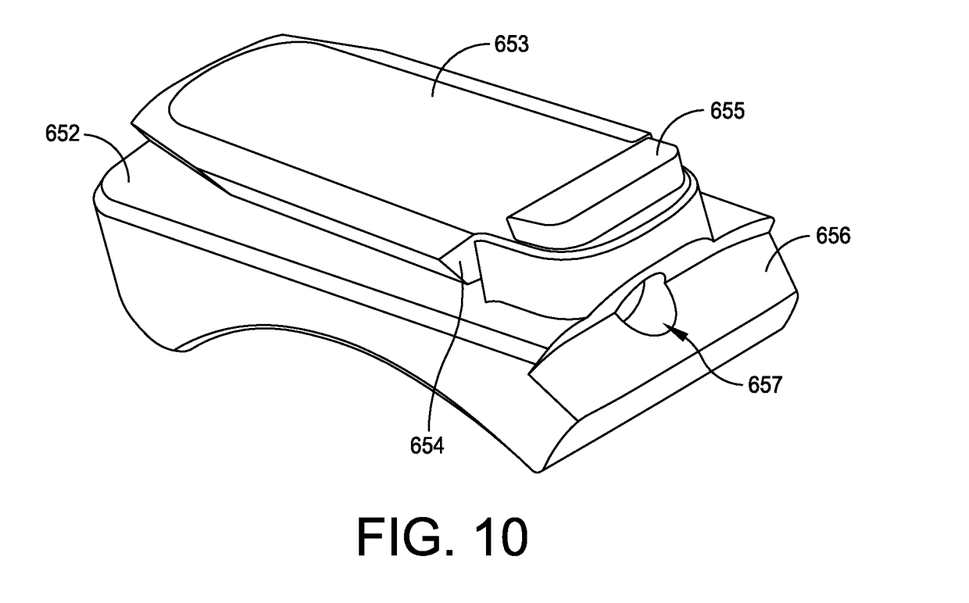
FIG. 10 is a top side view of a poly component.

FIG. 9 is an underside view and FIG. 10 is a top side view of the poly component 650. As shown in FIGS. 9 and 10, the poly component 650 can be substantially cubic with substantially flat sides and geometric features to engage and interface with surgical tooling, the tibial component 640, and the talar component 660. FIG. 9 shows that the inferior surface of the poly component 650 can include a recessed or concave surface 651 that defines an articulating surface to mate with a corresponding convex articulating surface of the talar component 660.

The superior side of the poly component 650 can include stepped surfaces that include a lower flat surface 652 that defines a substantially U-shape. When installed, the lower flat surface 652 will be adjacent to the inferior side 643 of the tibial component 640. FIG. 10 shows a protruding portion protruding from in between the legs of the U-shaped flat surface 652. A flat superior surface 653 defines most of the next stepped surface of the protruding portion. A U-shaped edge 654 of the protruding portion can be angled or chamfered to define a dovetail feature to fit within the corresponding undercut dovetail feature of the tibial component 640. A tab 655 with a flat top surface can protrude from the superior surface 653 and be configured to fit with the cavity 690 of the tibial component 640 and assist in locking together the poly component 650 and the tibial component 640 when the poly component 650 is installed.

The poly component 650 can also include an angled anterior notch 656 and a counterbore 657 on the anterior side both of which can be used to interface with tooling during the installation process. The poly component 650 can be made from or coated with a material that minimizes friction at the articular surface where the poly component 650 contacts the talar component 660. For example, the poly component 650 can be made from high-density polyethylene, polypropylene, or any other suitable material.

Figure 11:
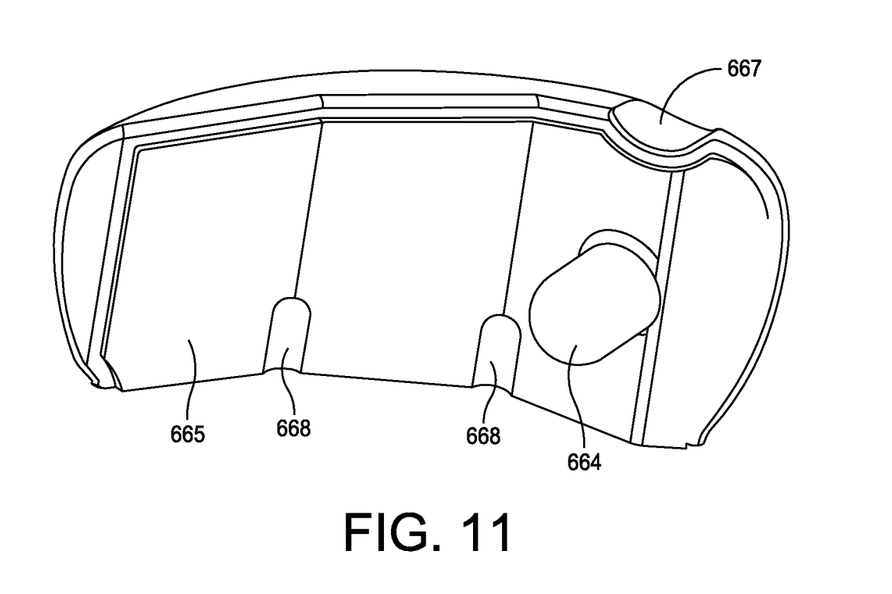
FIG. 11 is an underside view of the talar component 640 shown without the bioactive coating 670 and including grooves 668 and notch 667.

FIG. 11 is an underside view of the talar component 660 shown without the bioactive coating 670. As shown in FIGS. 7 and 11, the tibial component 640 can have a substantially curved or crescent shape to match the geometry of the talar dome of the talus bone.

FIG. 7 shows that the talar component 660 includes a single continuous dome-shaped superior surface 662 that can be smooth or polished to facilitate articulation with the poly component 650. Talar component 660 is connected to the talus bone with one or more talar anterior pegs 664 that are located within holes provided in the talus. As shown in FIG. 11, the talar component 660 can include a notch 667 defined in at least one side surface that extends between superior surface 662 and anterior surface 665. Notch 667 may be defined by an inwardly curved, e.g. semi-cylindrical, depression in the selected side surface, and is sized and oriented to provide an interface or pilot for engagement with a portion of a surgical assembly tool thereby allowing accurate alignment of the prosthesis by the surgeon during installation. Also, as shown in FIG. 11, the anterior surface 665 of the talar component 660 defines one or more grooves 668. Grooves 668 may be defined by an inwardly curved, e.g. semi-cylindrical, depression in anterior surface 665, and are often oriented transversely on anterior surface 665. Grooves 668 provide added surface area to increase advantageously bone adhesion with the patient's talus. Other orientations of grooves 668, e.g., longitudinal or angled relative to a longitudinal or transverse axis of talar component 660, may be defined on anterior surface 665 to provide improved adhesion.

Optionally, bone cement can be applied to portions of the talar component 660 to help secure the talar component 660 to the talus. Also, a talar implant impactor tool can be used to complete seating of the talar component 664 to the talus.

The talar component 660 can be made of a cobalt chrome alloy, stainless steel, titanium, titanium alloy, or any other suitable material. Optionally, the talar component 660 can be made using an additive manufacturing process such as 3-D printing. Optionally, the talar component 660 can be made to fit an individual patient.

Upon completion of a partial ankle replacement procedure, the tibial component 640 is connected to the tibia, with pegs 644 located within peg holes in the resected tibia. The talar component 660 is connected to the talus, with talar dome anterior pegs 664 located within holes in the resected talus. The poly component 650 is inserted and located between the tibial component 640 and the talar component 660.

The medial unicompartmental ankle prosthesis 300 shown in FIG. 3 can include similar tibial, poly, and talar components with the same features as those described with respect to the lateral unicompartmental ankle prosthesis 630. For example, the tibial component 640 and the poly component 650 of the lateral unicompartmental ankle prosthesis 630 can be interchangeable with the tibial component and the poly component, respectively, of the medial unicompartmental ankle prosthesis 300. Additionally, the talar component of the medial unicompartmental ankle prosthesis 300 can be a mirrored copy of the talar component 660 of the lateral unicompartmental ankle prosthesis 630 in that the placement of the notch 667 and grooves 668 to interface with assembly tools are on different sides of the talar component.

Figure 12:
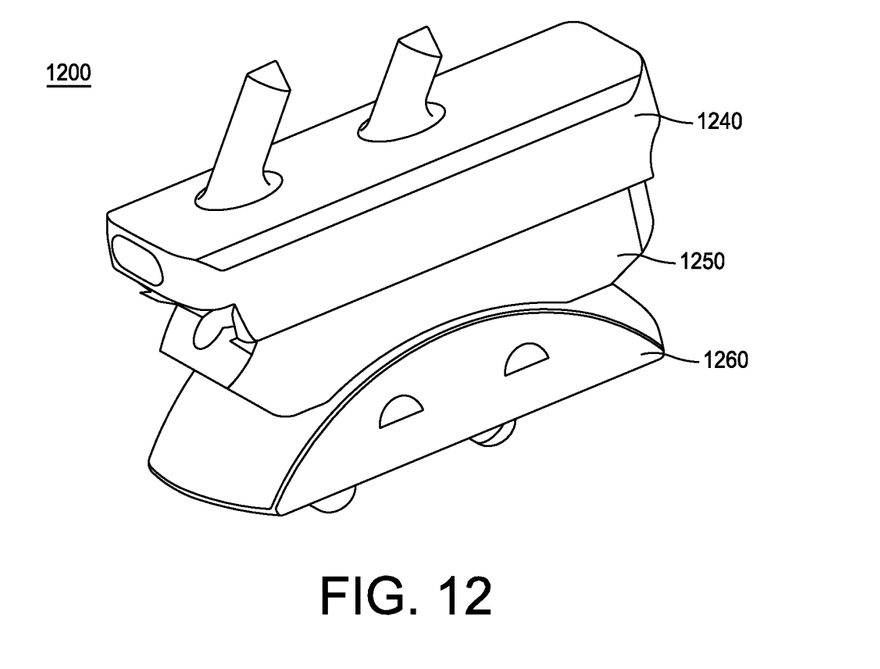
FIGS. 12 and 13 show another embodiment of a medial unicompartmental ankle prosthesis.
Figure 13:
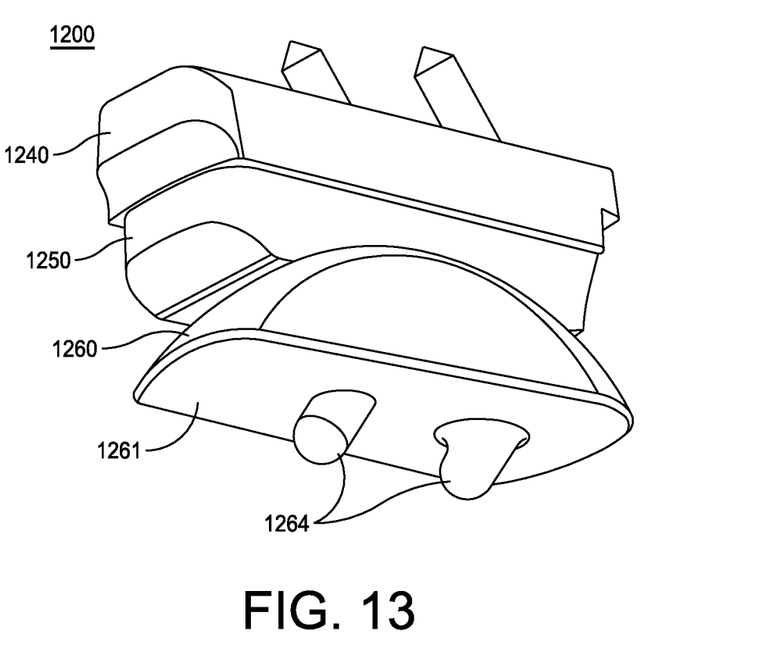

In another embodiment, a medial unicompartmental ankle prosthesis 1200 can include three components similar to that shown in FIGS. 12 and 13 and previously described. The medial unicompartmental ankle prosthesis 1200 can include a tibial component 1240, a poly component 1250, and a talar component 1260. While the tibial component 1240 and the poly component 1250 can include the same features or be interchangeable with the tibial component 640 and the poly component 650 described above, the talar component 1260 is different than the talar component 660.

FIGS. 12 and 13 show that the anterior surface 1261 of the talar component 1260 is flat. This can offer a surgical option to best fit a patient or in situations were more of the talus needs to be removed. Thus, the shape of the talar component 1260 is substantially hemispherical. The talar component 1260 is connected to the talus bone with one or more talar anterior pegs 1264 that are located within holes provided in the talus.

Although FIG. 3 shows medial and lateral unicompartmental ankle prostheses 300, 330 for a patient's right foot, the location for the two prostheses can also be switched on a patient's left foot. For example, the medial unicompartmental ankle prosthesis 300 for a right foot can be used as a lateral unicompartmental ankle prosthesis for a left foot. Likewise, the lateral unicompartmental ankle prosthesis 330 for a right foot can be used as a medial unicompartmental ankle prosthesis for a left foot. The difference between the medial and lateral unicompartmental ankle prostheses 300, 330 primarily being the mirrored location of the tooling interface features of the talar component 1260.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:
1. A partial ankle prosthesis comprising:
a tibial component including a superior surface configured to be attached to a lower end of a patient's tibia;
a poly component that is fixedly attached to the tibial component and includes a concave inferior surface of an anti-friction material; and
a talar component including an inferior surface configured to be attached to a patient's talus and a single convex superior surface configured to mate with the inferior surface of the poly component; wherein
the partial ankle prosthesis is configured to be implanted in a single compartment of a patient's ankle.

2. The partial ankle prosthesis of claim 1, wherein the superior surface of the tibial component includes a peg configured to fit into a hole in the patient's tibia.

3. The partial ankle prosthesis of claim 1, wherein the anterior surface of the talar component includes a peg configured to fit into a hole in the patient's talus.

4. The partial ankle prosthesis of claim 1, wherein the superior surface of the talar component has only one continuous concave curvature both longitudinally between opposite anterior and posterior ends and laterally between opposite medial and lateral sides.

5. The partial ankle prosthesis of claim 1, further comprising a bioactive coating on a surface of the tibial component and/or the talar component that interfaces with a patient's bone.

6. The partial ankle prosthesis of claim 1, wherein an inferior surface of the talar component is curved and configured to attach to a talar dome of the talus.

7. The partial ankle prosthesis of claim 1, wherein an inferior surface of the talar component is substantially flat.

8. The partial ankle prosthesis of claim 1, wherein the talar component defines a notch arranged so as to interface with a surgical assembly tool.

9. A partial ankle prosthesis comprising:
   a tibial component including a superior surface having an outwardly projecting peg configured to be received within a corresponding passageway formed in a portion of a distal tibia;
   a poly component that is fixedly attached to the tibial component and includes a concave inferior surface of an anti-friction material; and
   a talar component including an inferior surface having an outwardly projecting peg configured to be received within a corresponding passageway formed in a portion of a talus and a single convex superior surface configured to mate with the inferior surface of the poly component such that the partial ankle prosthesis may be implanted in a single compartment of a patient's ankle.

10. The partial ankle prosthesis of claim 9, wherein the anterior surface of the talar component defines at least groove so as to provide additional surface area and thereby increase bone adhesion.

11. The partial ankle prosthesis of claim 9, wherein the superior surface of the talar component has only one continuous concave curvature both longitudinally between opposite anterior and posterior ends and laterally between opposite medial and lateral sides.

12. The partial ankle prosthesis of any of claim 9, further comprising a bioactive coating on a surface of the tibial component and/or the talar component that interfaces with a patient's bone.

13. The partial ankle prosthesis of any of claim 9, wherein an inferior surface of the talar component is curved and configured to attach to a talar dome of the talus.

14. The partial ankle prosthesis of any of claim 9, wherein an inferior surface of the talar component is substantially flat.

15. The partial ankle prosthesis of claim 9, wherein the talar component defines a notch arranged so as to interface with a surgical assembly tool.

16. A partial ankle prosthesis comprising:
   a tibial component including a superior surface configured to be attached to a lower end of a patient's tibia;
   a poly component that is fixedly attached to the tibial component and includes a concave inferior surface of an anti-friction material; and
   a talar component including an inferior surface configured to be attached to a patient's talus and a single convex superior surface having one continuous concave curvature both longitudinally between anterior and posterior ends and laterally between medial and lateral sides, with a notch defined in at least one of the medial and lateral sides so as to interface with a surgical assembly tool, the partial prosthesis being configured to mate with the inferior surface of the poly component, such that the partial ankle prosthesis is configured to be implanted in a single compartment of a patient's ankle.

17. The partial ankle prosthesis of claim 16, wherein the superior surface of the tibial component includes a peg configured to fit into a hole in the patient's tibia.

18. The partial ankle prosthesis of claim 16, wherein the anterior surface of the talar component includes a peg configured to fit into a hole in the patient's talus.

19. The partial ankle prosthesis of claim 16, further comprising a bioactive coating on a surface of the tibial component and/or the talar component that interfaces with a patient's bone.

20. The partial ankle prosthesis of claim 16, wherein an inferior surface of the talar component is curved and configured to attach to a talar dome of the talus.

* * * * *